(12) United States Patent
Fayram et al.

(10) Patent No.: US 9,022,945 B2
(45) Date of Patent: May 5, 2015

(54) METHODS AND SYSTEMS THAT MONITOR FOR AN IMPENDING MYOCARDIAL INFARCTION

(71) Applicant: Pacesetter, Inc., Sunnyvale, CA (US)

(72) Inventors: Timothy A. Fayram, Gilroy, CA (US); Daniell Dokko, Mountain View, CA (US); Taraneh Ghaffari Farazi, San Jose, CA (US); Mark Carlson, Calabasas, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 0 days.

(21) Appl. No.: 14/172,776

(22) Filed: Feb. 4, 2014

(65) Prior Publication Data

US 2014/0155707 A1 Jun. 5, 2014

Related U.S. Application Data

(62) Division of application No. 12/499,738, filed on Jul. 8, 2009, now Pat. No. 8,672,855.

(51) Int. Cl.
*A61B 5/02* (2006.01)
*A61B 5/00* (2006.01)
(Continued)

(52) U.S. Cl.
CPC ............. *A61B 5/686* (2013.01); *A61B 5/0084* (2013.01); *A61B 5/02125* (2013.01); *A61B 5/026* (2013.01);
(Continued)

(58) Field of Classification Search
CPC ............. A61B 5/0215; A61B 5/02154; A61B 5/02007; A61B 5/0402; A61B 5/04012; A61B 5/026; A61B 5/0261; A61B 5/0285; A61B 5/0295; A61B 5/02416; A61B 5/686

USPC ........................................ 600/481, 507–509
See application file for complete search history.

(56) References Cited

U.S. PATENT DOCUMENTS 4,432,374 A  2/1984 Osanai
5,305,745 A  4/1994 Zacouto
(Continued)

FOREIGN PATENT DOCUMENTS

WO  2008017042 A1  2/2008
WO  2008112375 A2  9/2008
WO  2008112375 A3  9/2008

OTHER PUBLICATIONS

Chen et al. "Novel Compliance Index derived from digital volume pulse associated with risk factors and exercise capacity in patients undergoing treadmill exercise tests." Journal of Hypertension 2007, 25:1894-1899.*

(Continued)

*Primary Examiner* — Patricia Mallari
*Assistant Examiner* — Meredith Weare
(74) *Attorney, Agent, or Firm* — Theresa A. Raymer

(57) ABSTRACT

Implantable systems, and methods for use therewith, are provided for monitoring for an impending myocardial infarction. A signal indicative of changes in arterial blood volume is obtained. Such a signal can be a photoplethysmography signal or an impedance plethysmography signal. For each of a plurality of periods of time, a metric indicative of the areas under the curve of the signal or number of inflections in the signal is determined. An impending myocardial infarction is monitored for based on changes in the metric indicative of the area under the curve of the signal or number of inflections in the signal, and an alert and/or therapy is triggered in response to an impending myocardial infarction being predicted.

10 Claims, 11 Drawing Sheets

(51) Int. Cl.
| | |
|---|---|
| A61B 5/021 | (2006.01) |
| A61B 5/0295 | (2006.01) |
| A61B 5/1459 | (2006.01) |
| A61B 5/0205 | (2006.01) |
| A61B 5/0215 | (2006.01) |
| A61B 5/04 | (2006.01) |
| A61B 5/0402 | (2006.01) |
| A61B 5/026 | (2006.01) |
| A61B 5/053 | (2006.01) |
| A61N 1/365 | (2006.01) |
| A61B 5/024 | (2006.01) |

(52) U.S. Cl.
CPC .............. *A61B 5/0295* (2013.01); *A61B 5/0535* (2013.01); *A61B 5/0538* (2013.01); *A61B 5/1459* (2013.01); *A61N 1/36521* (2013.01); *A61N 1/36557* (2013.01); *A61B 5/7242* (2013.01); *A61B 5/02007* (2013.01); *A61B 5/0205* (2013.01); *A61B 5/02154* (2013.01); *A61B 5/02416* (2013.01); *A61B 5/04012* (2013.01); *A61B 5/0402* (2013.01); *A61B 5/4836* (2013.01); *A61B 5/746* (2013.01)

(56) References Cited

U.S. PATENT DOCUMENTS

| | | | | |
|---|---|---|---|---|
| 5,330,505 | A | | 7/1994 | Cohen |
| 5,409,009 | A | | 4/1995 | Olson |
| 5,603,329 | A | * | 2/1997 | Hosaka et al. ............. 600/493 |
| 5,730,125 | A | | 3/1998 | Prutchi |
| 5,941,837 | A | | 8/1999 | Amano |
| 6,063,036 | A | * | 5/2000 | Li ............................ 600/503 |
| 6,112,116 | A | | 8/2000 | Fischell |
| 6,272,379 | B1 | | 8/2001 | Fischell |
| 6,361,522 | B1 | | 3/2002 | Scheiner |
| 6,575,912 | B1 | | 6/2003 | Turcott |
| 6,824,561 | B2 | | 11/2004 | Soykan |
| 6,955,649 | B2 | * | 10/2005 | Narimatsu ................. 600/483 |
| 6,985,771 | B2 | | 1/2006 | Fischell |
| 7,181,269 | B1 | | 2/2007 | Kroll |
| 7,254,440 | B1 | | 8/2007 | Kroll |
| 7,277,745 | B2 | | 10/2007 | Natarajan |
| 7,481,759 | B2 | | 1/2009 | Whitehurst |
| 7,711,415 | B1 | | 5/2010 | Farazi |
| 7,887,502 | B2 | | 2/2011 | Ross |
| 2002/0137994 | A1 | | 9/2002 | Baker |
| 2003/0023175 | A1 | | 1/2003 | Arzbaecher |
| 2003/0036773 | A1 | | 2/2003 | Whitehurst |
| 2005/0065445 | A1 | | 3/2005 | Arzbaecher |
| 2006/0264771 | A1 | * | 11/2006 | Lin et al. ................... 600/513 |
| 2008/0027330 | A1 | * | 1/2008 | Naghavi et al. ............. 600/481 |
| 2008/0027341 | A1 | | 1/2008 | Sackner |
| 2008/0033260 | A1 | | 2/2008 | Sheppard |
| 2008/0067132 | A1 | | 3/2008 | Ross |
| 2008/0177194 | A1 | | 7/2008 | Zhang |
| 2008/0183091 | A1 | | 7/2008 | Fischell |
| 2008/0188760 | A1 | | 8/2008 | Al-Ali |
| 2008/0188763 | A1 | | 8/2008 | John |
| 2008/0228094 | A1 | * | 9/2008 | Audet et al. ............... 600/513 |
| 2009/0062667 | A1 | * | 3/2009 | Fayram et al. ............. 600/486 |
| 2009/0281399 | A1 | | 11/2009 | Keel |
| 2010/0022902 | A1 | | 1/2010 | Lee |
| 2010/0049060 | A1 | | 2/2010 | Schecter |
| 2010/0081941 | A1 | * | 4/2010 | Naghavi et al. ............. 600/481 |

OTHER PUBLICATIONS

Matthews, Robert J. "Peripherial Vascular Disease." Mar. 2, 2008. https://web.archive.org/web/20080302032944/http://www.rjmatthewsmd.com/Definitions/peripheral_vascular_disease.htm.*

Non-Final Office Action mailed Mar. 9, 2012: Related U.S. Appl. No. 12/499,738.

Non-Final Office Action mailed Sep. 14, 2012: Related U.S. Appl. No. 12/499,738.

Non-Final Office Action mailed Apr. 23, 2013: Related U.S. Appl. No. 12/499.738.

Final Office Action mailed Oct. 3, 2013: Related U.S. Appl. No. 12/499,738.

Notice of Allowance mailed Dec. 24, 2013 Related U.S. Appl. No. 12/499,738.

"Pulse Pressure Method and the Area Method for the Estimation of Total Arterial Compliance in Dogs: Sensitivity to Wave Reflection Intensity," Segers et al., Annals of Biomedical Engineering, vol. 27, pp. 480-485, 1999.

"Aortic Pulse Wave Velocity as a Marker of Cardiovascular Risk in Hypertensive Patients," Blacher et al., Hypertension 1999, 33:1111-1117.

"Increased Heart Rate as a Risk Factor for Cardiovascular Disease," Singh, B.N. European Heart Journal Supplements (2003) 5 (Supplement G), G3-G9.

"Pulse Pressure and Risk for Myocardial Infarction and Heart Failure in the Elderly," Vaccarino et al., Journal of the American College of Cardiology, vol. 36, No. 1, 2000.

"Pulse Wave Velocity and the Estimated Risk of Stroke and Myocardial infarction," Grodzicki et al., Acta Cardiol. Feb. 2002; 57(1):36-7.

"Vascular Compliance and Cardiovascular Disease," Glasser et al., Am J Hypertens. Oct. 1997; 10(10 Pt 1):1175-89.

"Novel Compliance Index Derived from Digital Volume Pulse Associated with Risk Factors and Exercise Capacity in Patients Undergoing Treadmill Exercise Tests," Chen et al., Journal of Hypertension 2007, 25:1894-1899.

\* cited by examiner

METHODS AND SYSTEMS THAT MONITOR FOR AN IMPENDING MYOCARDIAL INFARCTION

PRIORITY CLAIM

This application is a Divisional application of U.S. patent application Ser. No. 12/499,738, filed Jul. 8, 2009, entitled "METHODS AND SYSTEMS THAT MONITOR FOR AN IMPENDING MYOCARDIAL INFARCTION" which is incorporated herein by reference in its entirety to provide continuity of disclosure.

FIELD OF THE INVENTION

Embodiments of the present invention relate to implantable systems, and methods for use therewith, for detecting, recognizing, and treating a patient before the occurrence of a myocardial infarction (MI).

BACKGROUND OF THE INVENTION

A myocardial infarction (MI or AMI for acute myocardial infraction), commonly known as a heart attack, occurs when the blood supply to part of the heart is interrupted. This is most commonly due to occlusion (blockage) of a coronary artery following the rupture of a vulnerable atherosclerotic plaque. This occurs through years of an undetected or untreated combination of hypertension and abnormally high levels of lipids in a patient's blood. With time a patient builds up plaque deposits in the interior lining of their coronary arteries. This condition is commonly referred to as Coronary Artery Disease (CAD).

In some patients, these plaque deposits become severe enough that a restriction in coronary artery blood flow occurs and the patient becomes symptomatic. These restrictions can be clinically detected via various diagnostic and exercise tests. The patient begins to experience pain (angina) as well.

The typical treatment for this patient population is a Percutaneous Coronary Intervention (PCI), also known as Angioplasty. A balloon on the end of a catheter is inflated to remove the restricting plaque deposits, and then a stent is placed to stabilize the repaired region. In some cases, the restrictions are so extensive and severe that a Coronary Artery Bypass Graft (CABG) procedure is required. If detected and treated early enough, this patient group can avoid the deleterious effects resulting from a heart attack.

However, some patients are not as fortunate. These patients are asymptomatic. Their CAD remains undetected or untreated, and at a point in time, a region of the plaque becomes vulnerable and a surface layer of inflammation develops. The inflamed region can rupture, expelling plaque material (calcified deposits) into the coronary artery. Platelets in the blood stream recognize this foreign material and encapsulate it. A blood clot forms in close proximity or just downstream from the ruptured region. This leads to a devastating chain of events for the patient. The blockage in a coronary artery prevents the flow of blood that contains vital oxygen to the myocardial tissue supplied by that coronary artery. The patient begins to experience symptoms such as intense pain. Typical treatments are an immediate PCI procedure or an immediate transfusion of an anticoagulant or thrombolytic agent to break or dissolve the blood clot. Time is of the essence. If not treated immediately, the affected myocardium will not receive sufficient oxygen supply and that region of cardiac muscle will literally die. This is referred to as a Myocardial Infarction (MI), also known as a heart attack. If the patient survives, the MI can lead to further complications with time, including a susceptibility to tachyarrhythmias and a loss of heart function through the mechanisms of heart failure. The worst outcome is not surviving the heart attack. This can happen when the coronary artery blockage is so severe that the patient experiences a lethal arrhythmia and can not be resuscitated.

The challenge is to detect, recognize, and successfully treat the patient before a blockage of a coronary artery occurs. This is what the American Heart Association (AHA) refers to as Acute Coronary Syndrome (ACS). This could be done in advance of the life threatening MI or the subsequent tachyarrhythmias. Preventing the MI and protecting patients from dangerous arrhythmias would be clinically important. It would save many lives through prevention of a first heart attack, and could have profound implications in cost savings to our health care system. Many of the subsequent complications resulting from heart failure could be avoided as well.

SUMMARY OF THE INVENTION

Embodiments of the present invention are related to implantable systems, and methods for use therewith. Specific embodiments of the present invention relate to implantable systems that include an implantable sensor, and methods for use therewith.

Certain embodiments of the present invention relate to monitoring for an impending MI. In accordance with an embodiment, an implanted sensor is used to produce a signal that is indicative of changes in arterial blood volume. For a period of time a metric indicative of the area under the curve of the signal is determined. The sensor can be implanted subcutaneously in the pectoral region or it can be implanted elsewhere, such as the subcutaneous region of the abdomen. The signal indicative of changes in arterial blood volume can be a plethysmography signal such as a photo plethysmography signal or an impedance plethysmography signal. An impending MI is monitored for based on changes in the metric indicative of the area under the curve of the signal and an alert and/or therapy can be triggered in response to an impending MI being detected. In accordance with an embodiment, the above can be repeated from time to time. In accordance with an embodiment, the signal that is indicative of changes in arterial blood volume can be an averaged signal that can be produced by averaging a plurality of cardiac cycles of the signal obtained from the implanted sensor.

In accordance with an embodiment of the present invention, a plethysmography signal indicative of changes in arterial blood volume is produced and a metric indicative of the area under the curve can be determined for a plurality of periods of time. In accordance with an embodiment, a baseline of the metric indicative of area under the curve can be determined and an impending MI can be monitored for by comparing the determined metric indicative of the area under the curve to the baseline and predicting an impending MI if the determined metric indicative of the area under the curve falls below the baseline by at least a specified threshold. In accordance with an embodiment, predicting an impending MI includes distinguishing between an impending MI and a transient myocardial ischemic event based on a length of time that the metric indicative of the area under the curve falls below the baseline by at least the specified threshold. In accordance with an embodiment, an impending MI can be predicted if a decrease beyond a specified threshold is detected, in the metric indicative of the area under the curve of the plethysmography signal, from one of the periods of time to the immediately following one of the periods of time. In an embodiment, an impending MI can be predicted if a decrease by at least a specified amount for at least a specified period of time is detected.

Certain embodiments of the present invention relate to monitoring for an impending MI by monitoring changes in vascular stiffness based on changes in the area under the curve of a plethysmography signal. An impending MI can be predicted if an increase in vascular stiffness beyond a specified threshold is detected, or if an increase in vascular stiffness beyond a specified threshold is detected within a specified time period.

In accordance with an embodiment, the metric indicative of area under the curve can be selected from a group consisting of an integral, a width from the start to the end, and a full width at half maximum (FWHM) of a cycle of a signal indicative of changes in arterial blood volume. For each of the above, an average of the signal can be determined. The metric indicative of area under the curve can then be measured based on the average of the signal. In an embodiment of the present invention, the metric indicative of the area under the curve can be determined for each of a plurality of cycles of the signal, and then an average of those metrics can be determined.

Other embodiments for monitoring for an impending MI include using a chronically implanted device to produce a plethysmography signal that is indicative of changes in arterial blood volume. For each of a plurality of periods of time, a metric indicative of a number of inflections can be determined in the plethysmography signal for the period of time. An impending MI can be monitored for based on changes in the metric indicative of the number of inflections in the plethysmography signal. An alert and/or therapy can be triggered in response to an impending MI being detected. In an embodiment, the number of inflection can be determined, e.g., by determining a first or second derivative of the plethysmography signal and counting a number of zero crossings during a cycle of the plethysmography signal. This can be done after the signal is filtered, smoothed and/or averaged to get rid of inflections that are merely due to noise. The metric indicative of inflections can be number of peaks, number of positive peaks, or number of negative peaks in a cycle of a plethysmography signal, or number of zero crossing in the first derivative of the plethysmography signal, but is not limited thereto.

Certain embodiments of the present invention relate to monitoring for an impending MI with a chronically implanted device. A first signal indicative of changes in arterial blood volume can be obtained where the first signal can be, e.g., a photoplethysmography (PPG) signal or an impedance plethysmography (IPG) signal. A second signal indicative of electrical cardiac activity can also be obtained, where the second signal can be, e.g., an electrocardiogram (ECG) signal of an intracardiac electrogram (IEGM) signal. Based on the first and second signals, a metric indicative of aortic pulse wave velocity (PWV), diastolic blood pressure (DBP), heart rate (HR) and vascular stiffness can be determined. An impending MI can be monitored for based on the metrics indicative of PWV, DBP, HR and VS. An alert and/or therapy can be triggered in response to an impending MI being detected. In an embodiment, the metric indicative of PWV can be a peak pulse arrival time (PAT), peripheral pulse arrival time (PPAT) or PWV determined as a function of PAT or PPAT.

This description is not intended to be a complete description of, or limit the scope of, the invention. Other features, aspects, and objects of the various embodiments of the present invention can be obtained from a review of the specification, the figures, and the claims.

DETAILED DESCRIPTION OF THE INVENTION

Figure 1:
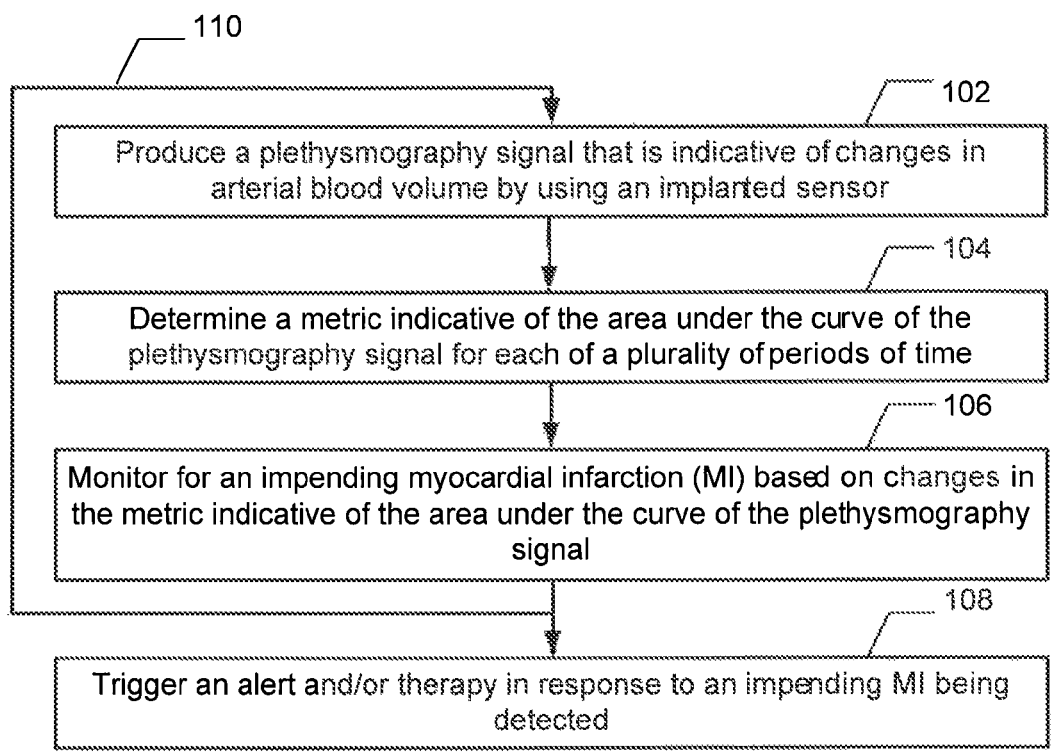
FIG. 1 is a high level flow diagram that is used to explain details for monitoring for an impending MI, in accordance with certain embodiments of the present invention.

The following description is of the best modes presently contemplated for practicing various embodiments of the present invention. The description is not to be taken in a limiting sense but is made merely for the purpose of describing the general principles of the invention. The scope of the invention should be ascertained with reference to the claims. In the description of the invention that follows, like numerals or reference designators will be used to refer to like steps, parts or elements throughout. In addition, the first digit of a reference number identifies the drawing in which the reference number first appears.

It would be apparent to one of skill in the art reading this description that the various embodiments of the present invention, as described below, may be implemented in many different embodiments of hardware, software, firmware, and/or the entities illustrated in the figures. Any actual software, firmware and/or hardware described herein is not limiting of the present invention. Thus, the operation and behavior of the embodiments of the present invention will be described with the understanding that modifications and variations of the embodiments are possible, given the level of detail presented herein.

Various embodiments of the present invention for predicting an impending MI will now be summarized beginning with a description of the high level flow diagrams of FIG. 1. Where embodiments of the present invention are summarized with reference to the high level flow diagrams, various algorithmic steps are summarized in individual 'blocks'. Such blocks describe specific actions or decisions that are made or carried out as the algorithm proceeds. Where a microcontroller (or equivalent) is employed, the flow diagrams presented herein provides the basis for a 'control program' that may be used by such a microcontroller (or equivalent) to effectuate the desired control of the implantable system. Those skilled in the art may readily write such a control program based on the flow diagram and other description presented herein. Embodiments of the present invention are not limited to the exact order and/or boundaries of the steps shown in the flow diagrams. In fact, many of the steps can be performed in a different order than shown, and many steps can be combined, or separated into multiple steps. All such variations are encompassed by the present invention. The only time order is important is where a step acts on the result of a previous step.

Referring to FIG. 1, at step 102, a plethysmography signal indicative of changes in arterial blood volume is obtained using an implanted extravascular sensor. For certain embodiments it is preferred that a plurality of cardiac cycles of the obtained plethysmography signal are averaged to produce a plethysmography signal that is an averaged plethysmography signal. At step 104 a metric indicative of the area under the curve of the plethysmography signal is determined for each of a plurality of periods of time. At step 106, based on changes in a metric indicative of the area under the curve of the plethysmography signal, an impending myocardial infarction is monitored for. In an embodiment of the present invention, monitoring for an impending MI includes distinguishing between an impending MI and a transient myocardial ischemic event, as will be explained below. At step 108, an alert and/or therapy can be triggered in response to an impending MI being detected.

As indicated by arrowed line 110, steps 102-106 are repeated from time to time, e.g., periodically, or in response to a triggering event. For example, steps 102-106 can be performed substantially continually, or periodically (e.g., once an hour, a day, a week, or the like). Additionally, steps 102-106 can be performed aperiodically, e.g., in response to a triggering event, many examples of which are discussed below.

In an embodiment of the present invention, the plethysmography signal indicative of changes in arterial blood volume can be a photoplethysmography (PPG) signal. Volume changes in blood vessels occur in a pulsatile manner with each beat of the heart as blood flows in and out of a portion of the body. A PPG sensor produces waveform measurements reflecting changes in arterial blood volume. These waveforms measurements are similar to arterial pressure waveform measurements because changes in arterial pressure correspond to relative changes in arterial blood volume. A metric indicative of the area under the curve of the PPG signal can be determined for each of a plurality of periods of time. For certain embodiments it is preferred that a plurality of cardiac cycles of the obtained PPG signal are averaged to produce a PPG waveform that is an averaged PPG waveform.

Exemplary PPG sensors are discussed below with reference to FIGS. 7A-7C. The PPG sensor can be implanted, e.g., in the pectoral region of a patient. Thus, it is practical that the PPG sensor can be integrated with or attached to the housing of a pacemaker or implantable cardioverter-defibrillator (ICD), as can be appreciated from FIGS. 7A and 8 discussed below. Alternative locations for implantation of the PPG sensor include, but are not limited to, the patient's abdomen.

In accordance with an embodiment of the present invention, the plethysmography signal indicative of changes in arterial blood volume can be an implanted impedance plethysmography (IPG) signal. An impedance plethysmography sensor can measure the change in arterial blood volume (venous blood volume as well as the pulsation of the arteries) for a specific body segment. As the arterial blood volume changes, the electrical impedance (resistance) also changes. A metric indicative of the area under the curve of the IPG signal is determined for each of a plurality of periods of time. For certain embodiments it is preferred that a plurality of cardiac cycles of the obtained IPG signal are averaged to produce an IPG signal that is an averaged IPG signal.

The IPG sensor can be implanted, e.g., in the pectoral region of a patient. Thus, it is practical that the IPG sensor can be integrated with or attached to the housing or a pacemaker or ICD, as can be appreciated from FIGS. 7A and 8 discussed below. Alternative locations for implantation of the IPG sensor include, but are not limited to, the patient's abdomen.

Figure 2A:
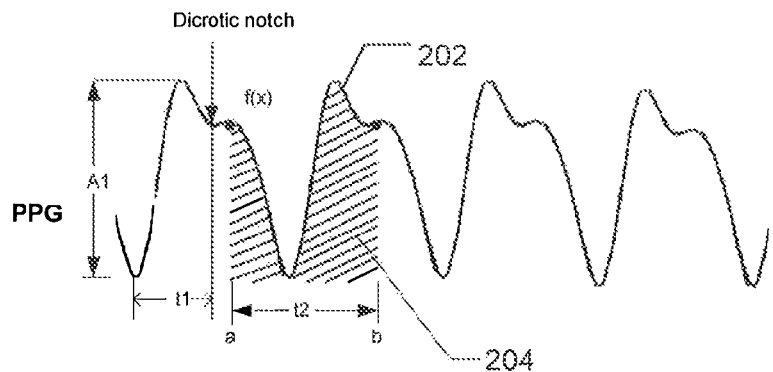
FIGS. 2A-2C includes exemplary PPG signal waveforms that are used to show various metrics that are indicative of the area under the curve.

FIG. 2A illustrates an exemplary PPG signal waveform 202 that is used to show various metrics indicative of area under the curve. The peak to peak amplitude of the PPG signal is designated as A1. The time from the rise of the PPG waveform to the dichrotic notch is designated as $t_1$. As shown in FIG. 2A, a metric indicative of area under signal 202 can be an integral 204 of at least one cycle (t2) of the plethysmography signal waveform. In an embodiment, the area can be determined by multiplying the amplitude of the PPG signal by the time from the rise of the PPG waveform to the dichrotic notch ($t_1$). This calculation can be normalized with time or a running aggregate area can be calculated.

Figure 2B:
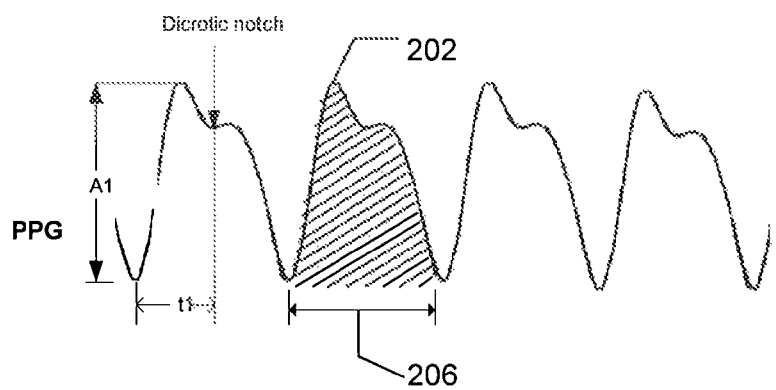
Figure 2C:
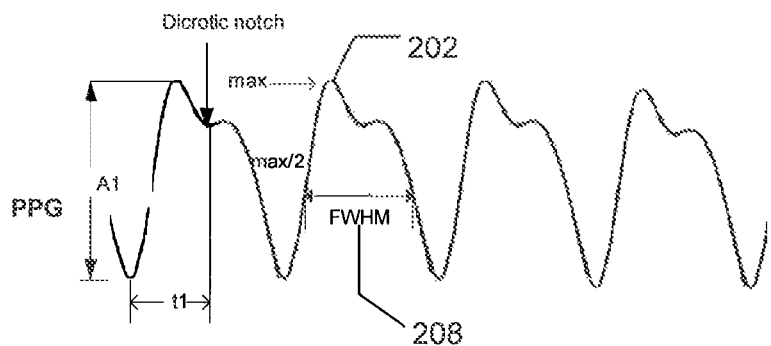

As shown in FIG. 2B, the metric indicative of area under curve 202 can also be a width 206 of a cycle of signal 202 where the width is measured from the start to the end of a cycle of a PPG signal. Additionally, as shown in FIG. 2C, a metric indicative of area under curve 202 can be a full width at half maximum (FWHM) 208 of a cycle of the PPG signal.

In accordance with an embodiment of the present invention, changes in the PPG waveform during a rupture of a region plaque within a coronary artery can be detected by using the area under the curve. For example, if the overall heart rate increases above a heart rate threshold, e.g., 120 beats per minute, and there is a significant reduction in the area under the PPG curve, then an acute event such as plaque rupture could be in process. In an embodiment of the present invention, the threshold can be a fixed threshold or a percentage, e.g., 150% or 175% of the patient's baseline heart rate.

Figure 3A:
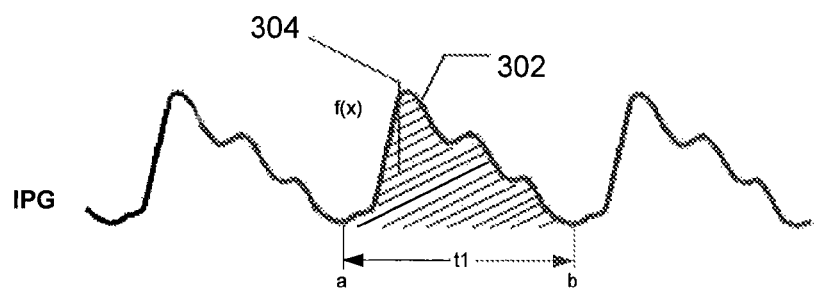
FIGS. 3A-3C includes exemplary IPG signal waveforms that are used to show various metrics that are indicative of the area under the curve.
Figure 3B:
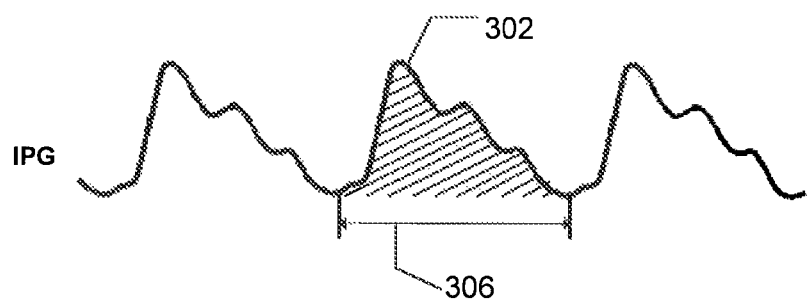
Figure 3C:
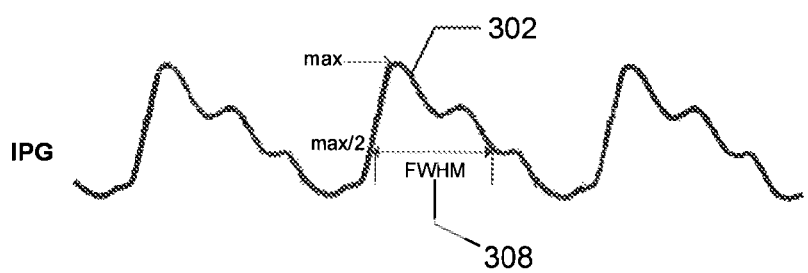

FIG. 3A illustrates an exemplary IPG signal waveform that is used to show various metrics indicative of area under the curve. As shown in FIG. 3A, a metric indicative of area under signal 302 can be an integral 304 of at least one cycle of the IPG signal. As an example, one cycle can be $t_1$ as shown in FIG. 3A. As shown in FIG. 3B, the metric indicative of area under curve 302 can also be a width 306 of a cycle of the signal 302, where the width is measured from the start to end of a cycle of an IPG signal. Additionally, as shown in FIG. 3C, a metric indicative of area under curve 302 can be a full width at half maximum 308 of the IPG signal.

Figure 4A:
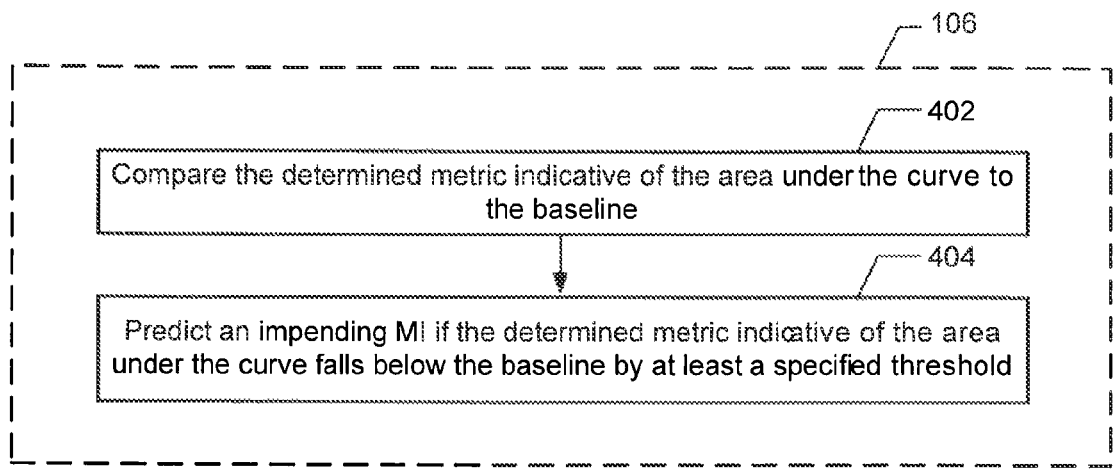
FIG. 4A is a flow diagram that is used to explain details of one of the steps (i.e., step 106) of the flow diagram of FIG. 1, according to an embodiment of the invention.

FIG. 4A is a flow diagram that is used to explain details of one of the steps (i.e., step 106) of the flow diagram of FIG. 1, according to an embodiment of the invention. At step 402 the metrics indicative of the area under the curve are compared to a baseline. The baseline can be determined by monitoring for the metric indicative of the area under the curve when a patient is not experiencing an MI. If the determined metric indicative of the area under the curve falls below the baseline by at least a specified threshold, an impending MI can be predicted. As an example, the specified threshold can be a percentage of the baseline or a predetermined value, but is not limited thereto.

Figure 4B:
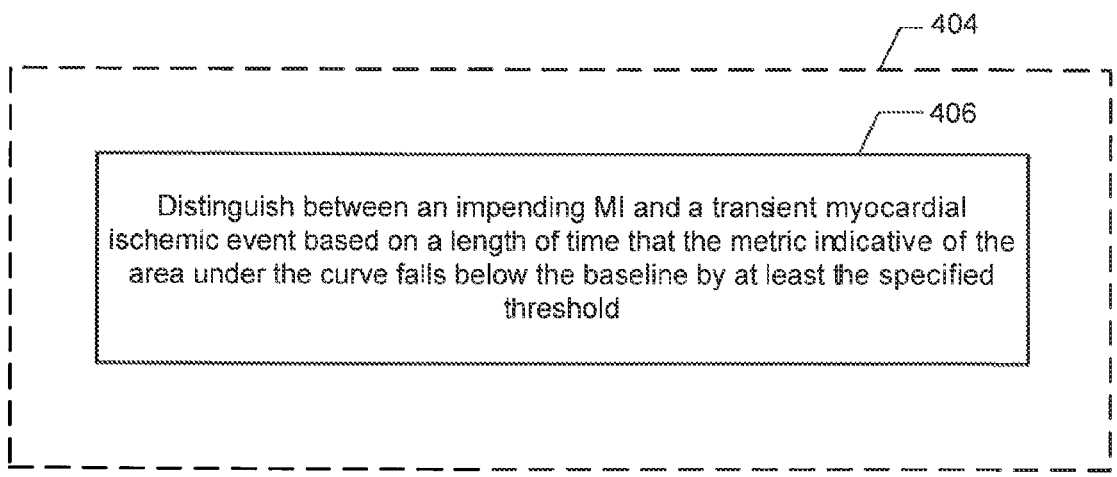
FIG. 4B is a flow diagram that is used to explain details of one of the steps (i.e., step 404) of the flow diagram of FIG. 4A, according to an embodiment of the invention.

FIG. 4B is a flow diagram that is used to explain details of one of the steps (i.e., step 404) of the flow diagram of FIG. 4A, according to an embodiment of the invention. At step 406 an impending MI and a transient myocardial ischemic event are distinguished between based on a length of time that the metric indicative of the area under the curve falls below the baseline by at least a specified threshold. The length of time can be, for example, set at a level (e.g., 15 minutes or some other defined period of time) that will help distinguish a transient ischemic event from an impending MI. In an embodiment of the invention, it can be expected that an ischemic event will result in a reduction in area under the curve for a relatively shorter period of time as compared to an impending MI. In an embodiment of the present invention, an impending MI is predicted if the metric indicative of the area under the curve of the plethysmography signal decreases by at least a specified amount for at least a specified period of time (e.g., by at least 30 percent, for at least 30 minutes). Otherwise, the detected event that caused the decrease in the area under the curve of the plethysmography signal is classified as a transient ischemic event.

Figure 4C:
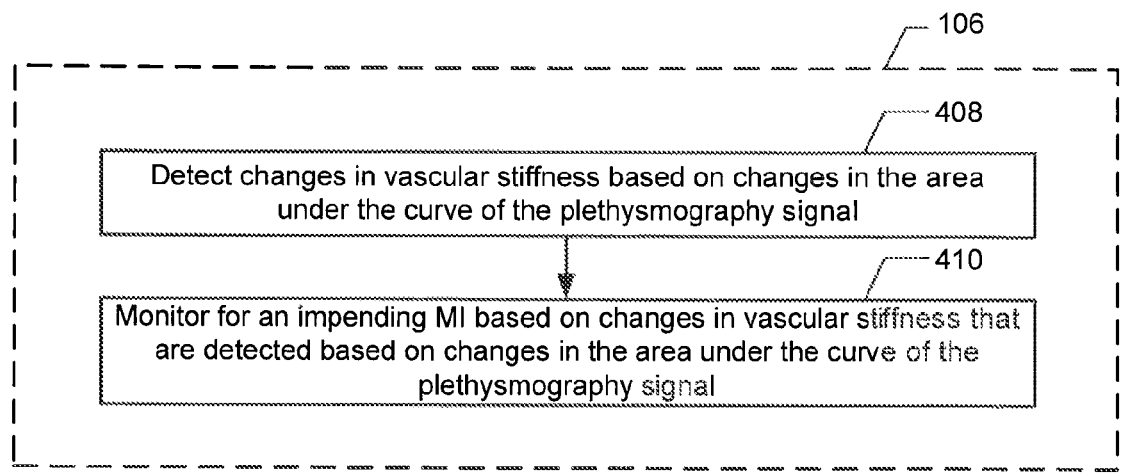
FIG. 4C is a flow diagram that is used to explain further details of one of the steps (i.e., step 106) of the flow diagram of FIG. 1, according to an alternate embodiment of the invention.

FIG. 4C is a flow diagram that is used to explain further details of one of the steps (i.e., step 106) of the flow diagram of FIG. 1, according to an alternate embodiment of the invention. At step 408 a change in vascular stiffness is detected based on changes in the area under the curve of the plethysmography signal. For example, a reduction in the area under the curve can result in an increase in vascular stiffness. At step 410 an impending MI is monitored for based on changes in vascular stiffness that are based on changes in the area under the curve of the plethysmography signal. In an embodiment of the invention, an impending MI is predicted if an increase in vascular stiffness is detected beyond a specified threshold and/or if an increase in vascular stiffness beyond a specified threshold is detected within a specified time period.

Figure 5A:
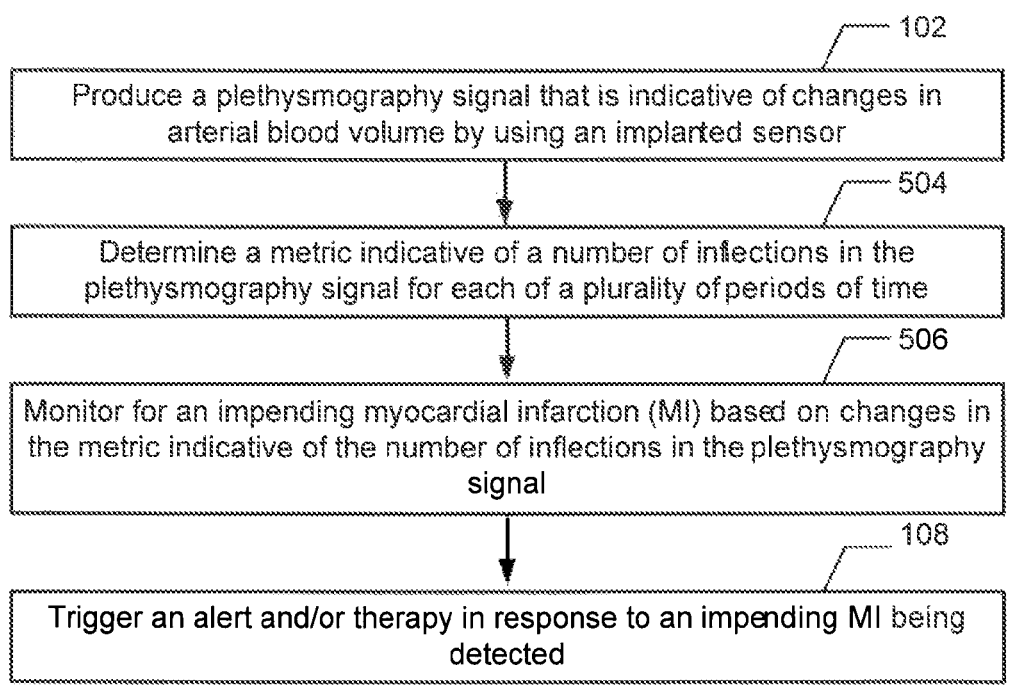
FIG. 5A is a flow diagram that is used to explain details for monitoring for an impending MI based on a number of inflections in a plethysmography signal.

FIG. 5A is a flow diagram that is used to explain details for monitoring for an impending MI based on a number of inflections in a plethysmography signal. In step 102 a plethysmography signal is produced that is indicative of changes in arterial blood volume by using an implanted sensor. In step 504 a metric indicative of a number of inflections in the plethysmography signal is determined for each of a plurality of periods of time. In step 506 an impending MI is monitored for based on changes in the metric indicative of the number of inflections in the plethysmography signal. In step 108 an alert and/or therapy is triggered in response to an impending MI being detected.

The technique described with reference to FIG. 5 can be performed by a chronically implanted device, examples of which are discussed below. The device can use an implanted sensor to produce the plethysmography signal that is indicative of changes in arterial blood volume. For each of a plurality of periods of time, the device can determine a metric indicative of a number of inflections in the plethysmography signal for the period of time. The metric indicative of inflections can be, e.g., number of peaks, number of positive peaks, or number of negative peaks in a cycle of a plethysmography signal. The number of inflections can be determined, for example, by determining a first or second derivative of the plethysmography signal and counting a number of zero crossings during a cycle of the plethysmography signal. In a specific embodiment, the number of inflections can be determined after the signal is filtered, smoothed, and/or averaged to get rid of inflections that are merely due to noise.

Figure 5B:
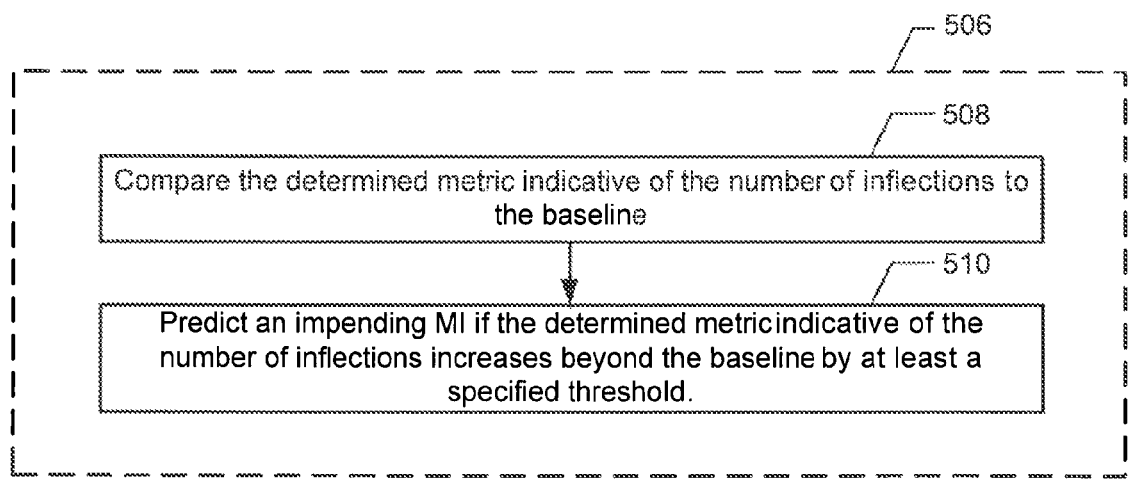
FIG. 5B is a flow diagram that is used to explain details of one of the steps step 506) of the flow diagram of FIG. 5A, according to an embodiment of the invention.

FIG. 5B is a flow diagram that is used to explain details of one of the steps (i.e., step 506) of the flow diagram of FIG. 5A, according to an embodiment of the invention. In step 508 an impending MI can be monitored for based on changes in the metric indicative of the number of inflections in the plethysmography signal once a metric indicative of a number of inflections in the plethysmography signal has been determined. For example, an impending MI can be detected by determining a baseline of the metric indicative of the number of inflections in the plethysmography signal when a patient is not experiencing an MI and thereafter comparing the determined metric indicative of the number of inflections to the baseline. In step 510 an impending MI can be predicted if the determined metric indicative of the number of inflections increases beyond the baseline by at least a specified threshold.

In certain embodiments, detecting an impending MI can also include distinguishing between an impending MI and a transient myocardial ischemic event based on a length of time that the metric indicative of the number of inflections remains increased beyond the baseline by at least the specified threshold. Because it is expected that an ischemic event will result in an increase in the number of inflections for only a relatively short period of time, the length of time is set at a level that will help distinguish an ischemic event from an impending MI.

In accordance with an embodiment of the present invention, an impending MI is predicted if an increase beyond a specified threshold is detected, in the metric indicative of the number of inflections in the plethysmography signal, from one of the periods of time to the immediately following one of the periods of time. In an embodiment of the invention, an impending MI can be predicted if the metric indicative of the number of inflections in the plethysmography signal increases by at least a specified amount for at least a specified period of time. For example, an impending MI can be predicted if the metric indicative of the number of inflections in the plethysmography signal increases by at least 30 percent, for at least 15 minutes, or some other defined percentage or period of time. The above percentage and time suggestions are exemplary and are not made to be taken as limiting.

Certain embodiments of the present invention relate to an implantable system configured to monitor for an impending MI. The system includes an implantable sensor to produce a plethysmography signal that is indicative of changes in arterial blood volume. A monitor can be configured to determine a metric indicative of the area under the curve of the plethysmography signal for each of a plurality of periods of time. The monitor can also be configured to monitor for an impending MI based on changes in the metric indicative of the area under the curve of the plethysmography signal. In an embodiment of the present invention, the monitor can be configured to determine a metric indicative of a number of inflections in the plethysmography signal for each of a plurality of the periods of time and monitor for an impending MI based on changes in the metric indicative of the number of inflections in the plethysmography signal.

In an embodiment of the present invention, the monitor can be configured to monitor for an impending MI, based of changes in the metric indicative of the area under the curve of the plethysmography signal, by comparing the determined metrics indicative of the area under the curve to a baseline, and predicting an impending MI if the determined metric indicative of the area under the curve falls below the baseline by at least a specified threshold. In an embodiment of the invention, the threshold can be set at a level that will help distinguish an ischemic event from an impending MI, because it is expected that an ischemic event will result in a relatively smaller reduction in area under the curve.

In an embodiment of the present invention, the monitor can be configured to monitor for an impending MI, based on changes in the metric indicative of the number of inflections in the plethysmography signal, by comparing the determined metrics indicative of the number of inflections to a baseline, and predicting an impending MI if the determined metric indicative of the number of inflections increases above the baseline by at least a specified threshold.

Figure 6:
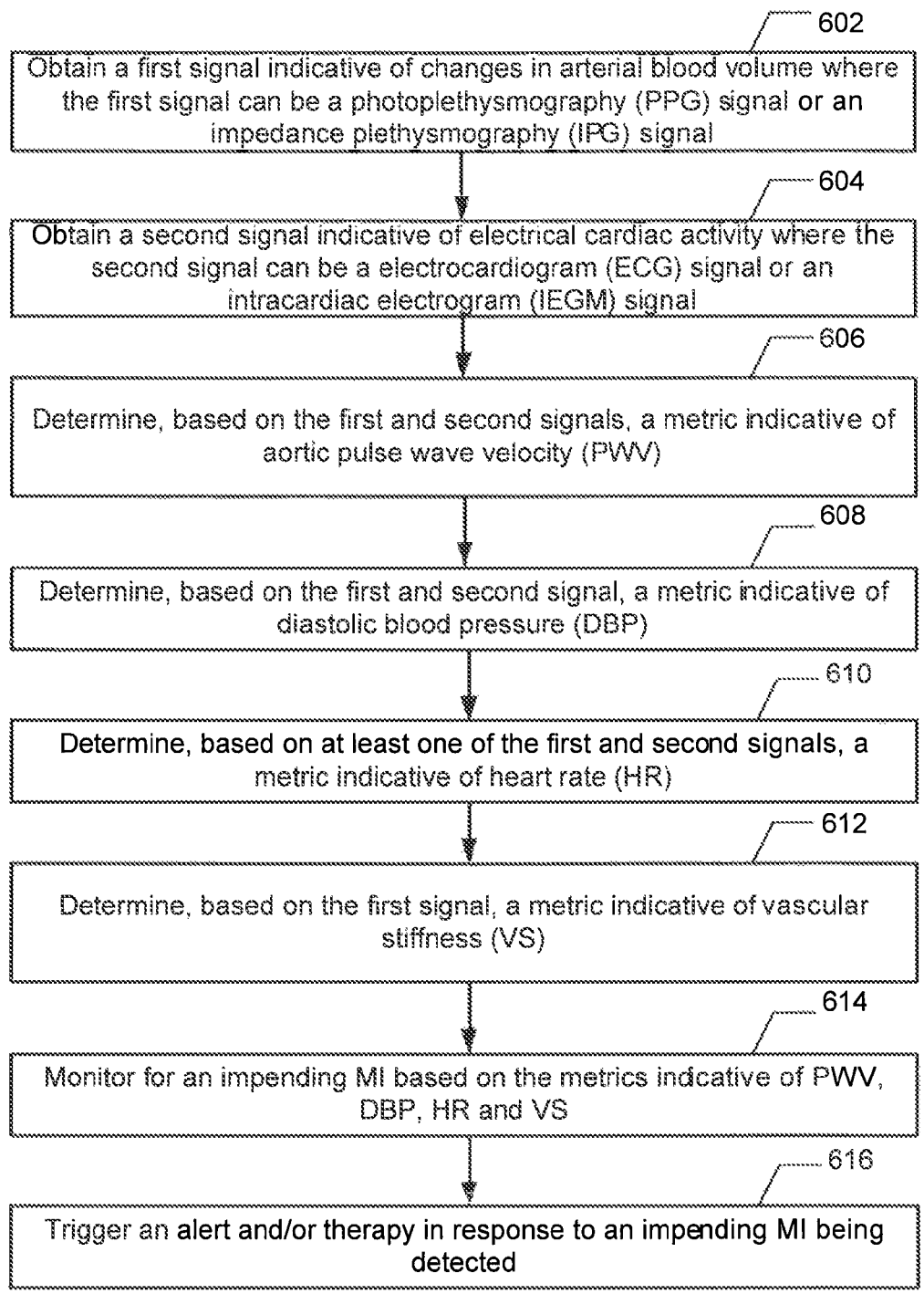
FIG. 6 is a flow diagram that is used to explain details for monitoring for an impending MI, in accordance with certain embodiments of the present invention.

FIG. 6 is a flow diagram that is used to explain details for monitoring for an impending MI, in accordance with certain embodiments of the present invention. At step 602 a first signal indicative of changes in arterial blood volume is obtained, where the first signal can be, e.g., a photoplethysmography (PPG) signal or an impedance plethysmography (IPG) signal. At step 604 a second signal indicative of electrical cardiac activity is obtained, where the second signal can be, e.g., an electrocardiogram (ECG) signal or an intracardiac electrogram (IEGM) signal. At step 606, based on the first and second signals, a metric indicative of aortic pulse wave velocity (PWV), diastolic blood pressure (DBP), heart rate (HR) and vascular stiffness can be determined.

In an embodiment of the invention, Pulse Wave Velocity (PWV) can be an indicator of vascular stiffness. The PWV measurement is the velocity of the pulse wave between two points as measured by two transducers located at reference points outside of the arterial system. This is typically measured at the Aorta. PWV is strongly associated with the presence and extent of atherosclerosis and constitutes a forceful marker and predictor of cardiovascular risk. In an embodiment, the number of peaks in the plethysmography signal can be used as surrogates of vascular stiffness. For example, the higher the number of peaks per cardiac signal, the stiffer the vasculature.

In an embodiment of the present invention, the metric indicative of PWV can be a Pulse Arrival Time (PAT), PPAT, or PWV determined as a function of PAT or PPAT, while the metric indicative of vascular stiffness can be a measure of the area under the curve of the first signal or the number of inflections in the first signal, but is not limited thereto. U.S. patent application Ser. No. 11/848,586, entitled "IMPLANTABLE SYSTEMIC BLOOD PRESSURE MEASUREMENT SYSTEMS AND METHODS" (Fayram et al.), filed on Aug. 31, 2007, which is incorporated herein by reference, provides exemplary details of how metrics indicative of PWV and DBP can be determined on the first and second signals.

At steps 608-612, based on the first signal and/or second signal, metrics indicative of diastolic blood pressure (DBP), heart rate (HR), and vascular stiffness (VS) can be determined. At step 614 an impending MI can be monitored for based on the metrics indicative of PWV, DBP, HR and VS. At step 616 an alert and/or therapy can be triggered in response to an impending MI being detected.

In the event of an impending MI, it is believed that PWV, DBP, VS and HR should all increase. Thus, when an increase in each of PWV, DBP, VS and HR beyond a corresponding threshold is detected, an alert and/or therapy can be triggered signaling an impending MI. In an embodiment, an impending MI can be detected if a majority of the metrics indicative of PWV, DBP, HR and VS exceed there corresponding threshold.

Exemplary Implantable System

Figure 7A:
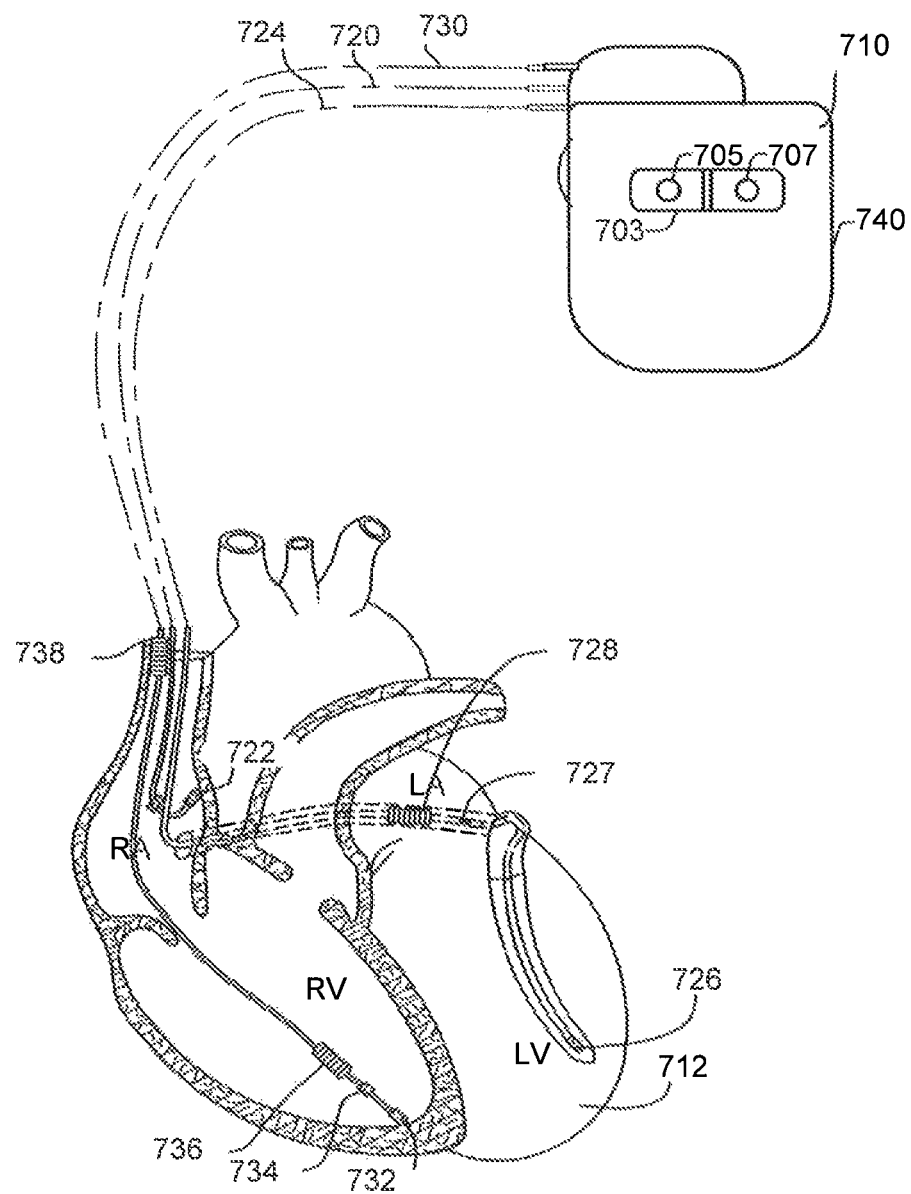
FIG. 7A illustrates an exemplary implantable stimulation device that can be used to perform various embodiments of the present invention.
Figure 7B:
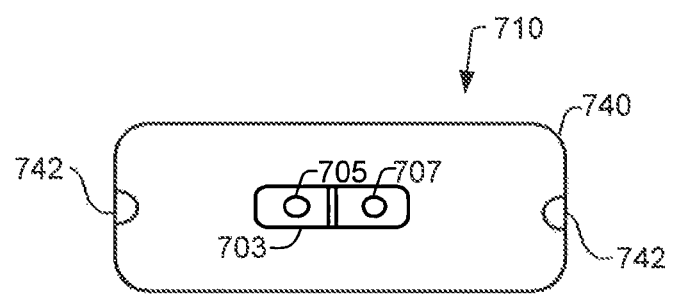
FIGS. 7B and 7C illustrate exemplary implantable monitoring devices that can be used to perform various embodiments of the present invention.
Figure 7C:
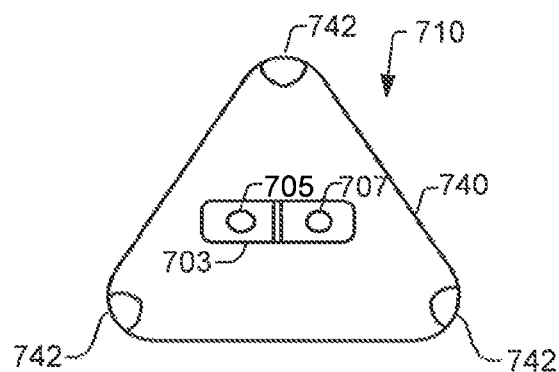

FIGS. 7A-7C and 8 will now be used to describe exemplary implantable systems that can be used to monitor for an impending MI, in accordance with embodiments of the present invention. Referring to FIG. 7A, the implantable system is shown as including an implantable stimulation device 710, which can be a pacing device and/or an implantable cardioverter defibrillator. The device 710 is shown as being in electrical communication with a patient's heart 712 by way of three leads, 720, 724 and 730, which can be suitable for delivering multi-chamber stimulation and shock therapy. The leads can also be used to obtain IEGM signals, for use in embodiments of the present invention. Instead of having leads with electrodes attached to the heart, it is also possible that subcutaneous electrodes can be used to obtain ECG signals. In still other embodiments, it's possible that the electrodes are located on the housing of the implantable device 710, and that such electrodes are used to obtain subcutaneous ECG signals. In this latter embodiment, the device 710 may not be capable of pacing and/or defibrillation, but rather, the implantable device 710 can be primarily for monitoring purposes.

The implantable system is also shown as including an implantable photoplethysmography (PPG) sensor 703 that can be used to produce a PPG signal, similar to signal 202 shown in FIGS. 2A-2C. Referring to FIG. 7A, the PPG 703 sensor includes a light source 705 and a light detector 707. The light source 705 can include, e.g., at least one light-emitting diode (LED), incandescent lamp or laser diode. The light detector 707 can include, e.g., at least one photoresistor, photodiode, phototransistor, photodarlington or avalanche photodiode. Light detectors are often also referred to as photodetectors or photocells.

The light source 705 outputs light that is reflected or back-scattered by surrounding patient tissue, and reflected/back-scattered light is received by the light detector 707. In this manner, changes in reflected light intensity are detected by the light detector, which outputs a signal indicative of the changes in detected light. The output of the light detector can be filtered and amplified. The signal can also be converted to a digital signal using an analog to digital converter, if the PPG signal is to be analyzed in the digital domain. Additional details of exemplary implantable PPG sensors are disclosed in U.S. Pat. Nos. 6,409,675 and 6,491,639, both entitled "Extravascular Hemodynamic Sensor" (both Turcott), which are incorporated herein by reference.

A PPG sensor can use a single wavelength of light, or a broad spectrum of many wavelengths. In the alternate embodiments, the light source can be any source of radiant energy, including laser diode, heated filament, and ultrasound transducer. The detector can be any detector of radiant energy, including phototransistor, photodetector, ultrasound transducer, piezoelectric material, and thermoelectric material.

It is generally the output of the photodetector that is used to produce a PPG signal. However, there exist techniques where the output of the photodetector is maintained relatively constant by modulating the drive signal used to drive the light source, in which case the PPG signal is produced using the drive signal, as explained in U.S. Pat. No. 6,731,967, entitled "Methods and Devices for Vascular Plethysmography via Modulation of Source Intensity," (Turcott), which is incorporated herein by reference.

The PPG sensor 703 can be attached to a housing 740 of an implantable device, which as mentioned above can be, e.g., a pacemaker and/or an implantable cardioverter-defibrillator (ICD), or a simple monitoring device. Exemplary details of how to attach a sensor module to an implantable cardiac stimulation device are described in U.S. patent application Ser. No. 10/913,942, entitled "Autonomous Sensor Modules for Patient Monitoring" (Turcott et al.), filed Aug. 4, 2004, which is incorporated herein by reference. It is also possible that the PPG sensor 703 be integrally part of the implantable cardiac stimulation device 710. For example, the PPG sensor 703 can be located within the housing 740 of an ICD (or pacemaker) that has a window through which light can be transmitted and detected. In a specific embodiment, the PPG sensor 703 has a titanium frame with a light transparent quartz window that can be welded into a corresponding slot cut in the housing of the ICD. This will insure that the ICD enclosure with the welded PPG sensor will maintain a hermetic condition. In alternative embodiments, the PPG sensor can be remote from housing 740 and can communicate with components within the housing via a bus (e.g., including one or more wires), or wirelessly, but is not limited thereto.

Where the PPG sensor 703 is incorporated into or attached to a chronically implantable device 710, the light source 705 and the light detector 707 can be mounted adjacent to one another on the housing or header of the implantable device. The light source 705 and the light detector 707 are preferably placed on the side of the implantable device 710 that, following implantation, faces the chest wall, and are configured such that light cannot pass directly from the source to the detector. The placement on the side of the device 710 that faces the chest wall maximizes the signal to noise ratio by directing the signal toward the highly vascularized musculature, and shielding the source and detector from ambient light that enters the body through the skin. Alternatively, at the risk of increasing susceptibility to ambient light, the light source 705 and the light detector 707 can be placed on the face of the device 710 that faces the skin of the patient.

The implantable PPG sensor 703 outputs a PPG signal similar to signal 202 shown in FIGS. 2A-2C. More specifically, the output of the light detector 705 can be an analog signal that resembles signal 202. Such a signal can be filtered and/or amplified as appropriate, e.g., to remove respiratory affects on the signal, and the like. Additionally, the signal can be digitized using an analog to digital converter. Based on the PPG signal (and in some embodiments an ECG or IEGM obtained using implanted electrodes) metrics indicative of area under the curve, number of inflections, vascular stiffness, PWV, DBP and/or HR can be determined, in accordance with embodiments of the present invention.

Still referring to FIG. 7A, to sense atrial cardiac signals and to provide right atrial chamber stimulation therapy, the device 710 is coupled to an implantable right atrial lead 720 having at least an atrial tip electrode 722, which typically is implanted in the patient's right atrial appendage. To sense left atrial and ventricular cardiac signals and to provide left-chamber pacing therapy, the device 710 is coupled to a "coronary sinus" lead 724 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 724 is designed to receive atrial and ventricular cardiac signals and to deliver left ventricular pacing therapy using at least a left ventricular tip electrode 726, left atrial pacing therapy using at least a left atrial ring electrode 727, and shocking therapy using at least a left atrial coil electrode 728.

The device 710 is also shown in electrical communication with the patient's heart 712 by way of an implantable right ventricular lead 730 having, in this embodiment, a right ventricular tip electrode 732, a right ventricular ring electrode 734, a right ventricular (RV) coil electrode 736, and an SVC coil electrode 738. Typically, the right ventricular lead 730 is transvenously inserted into the heart 712 so as to place the right ventricular tip electrode 732 in the right ventricular apex so that the RV coil electrode 736 will be positioned in the right ventricle and the SVC coil electrode 738 will be positioned in the superior vena cava. Accordingly, the right ventricular lead 730 is capable of receiving cardiac signals and delivering stimulation in the form of pacing and shock therapy to the right ventricle.

FIG. 7B illustrates an alternative embodiment of the implantable device 710. Here the housing 740 of the device is shown as small, thin, and oblong, with smooth surfaces and a physiologic contour which minimizes tissue trauma and inflammation. The oblong geometry of the housing 740 is desirable because it maximizes separation of electrodes 742 and prevents rotation of the monitor within the tissue pocket, thereby allowing interpretation of morphology features in an ECG sensed using electrodes 742. Two ECG electrodes 742 are shown, however more can be present. In the alternate embodiment illustrated in FIG. 7C, three ECG electrodes 742 are present, one at each apex of the triangle formed by the device housing 740. These three electrodes allow the three standard surface ECG leads I-III to be approximated. In an embodiment, four or more ECG electrodes might be used, with each orthogonal electrode pair providing orthogonal ECG signals. Alternatively, an embodiment lacking ECG electrodes is possible. A further alternative has a single ECG electrode with the monitor housing acting as the other electrode in the pair. U.S. Pat. No. 6,409,675, which was incorporated above by reference, provides some additional details of an implantable monitor that includes ECG electrodes on its housing and a PPG sensor. FIGS. 7B and 7C show that the implantable device 710 also include a PPG sensor 703.

Figure 8:
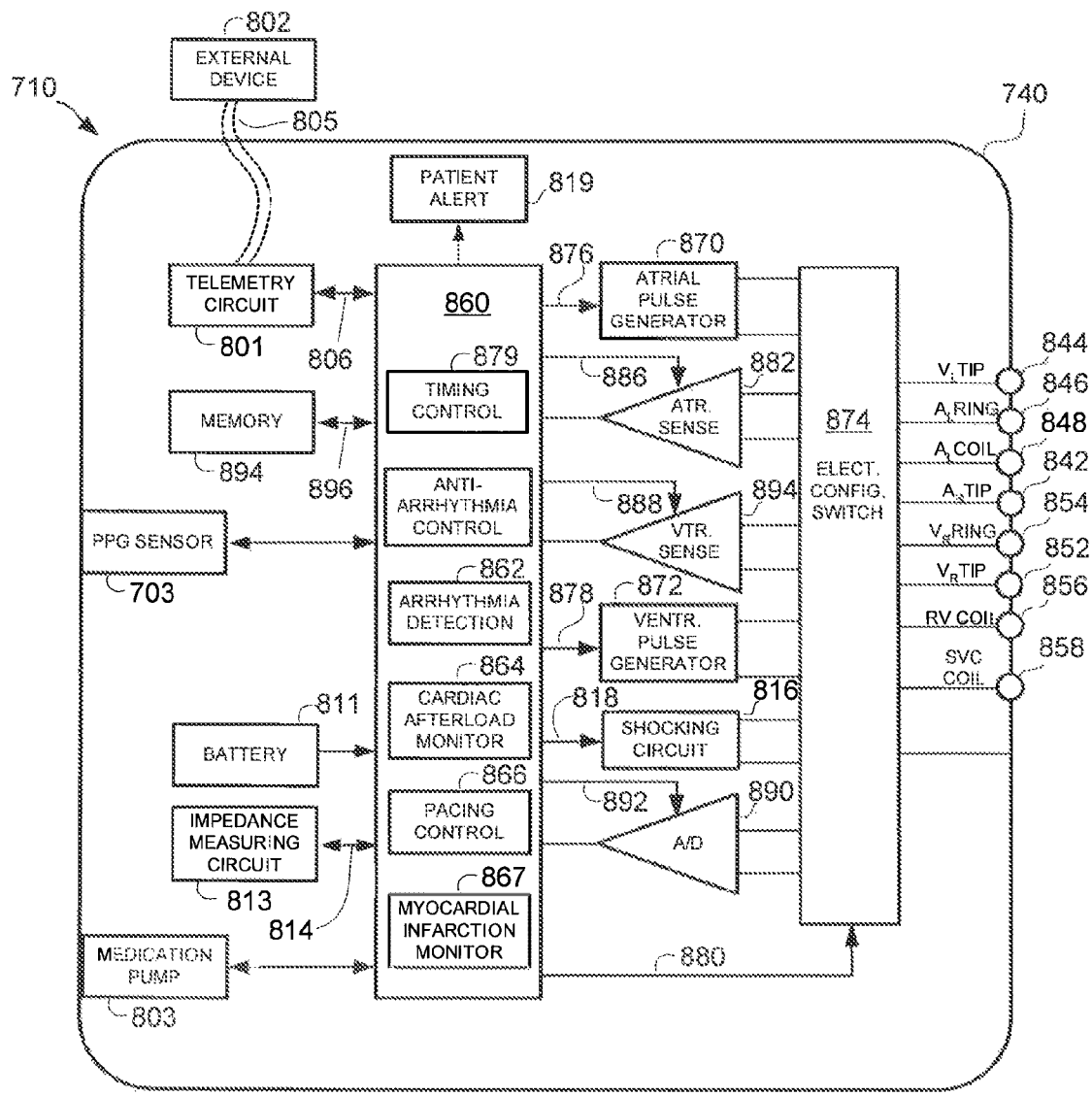
FIG. 8 is a simplified block diagram that illustrates possible components of the implantable devices shown in FIGS. 7A-7C.

FIG. 8 will now be used to provide some exemplary details of the components of the implantable devices 710. Referring now to FIG. 8, each of the above implantable devices 710, and alternative versions thereof, can include a microcontroller 860. As is well known in the art, the microcontroller 860 typically includes a microprocessor, or equivalent control circuitry, and can further include RAM or ROM memory, logic and timing circuitry, state machine circuitry, and I/O circuitry. Typically, the microcontroller 860 includes the ability to process or monitor input signals (data) as controlled by a program code stored in a designated block of memory. The details of the design of the microcontroller 860 are not critical to the present invention. Rather, any suitable microcontroller 860 can be used to carry out the functions described herein. The use of microprocessor-based control circuits for performing timing and data analysis functions are well known in the art. In specific embodiments of the present invention, the microcontroller 860 performs some or all of the steps associated with monitoring for an impending MI. Additionally, the microcontroller 860 may detect arrhythmias, and select and control delivery of anti-arrhythmia therapy.

Representative types of control circuitry that may be used with the invention include the microprocessor-based control system of U.S. Pat. No. 4,940,052 (Mann et. al.) and the state-machines of U.S. Pat. No. 4,712,555 (Sholder) and U.S. Pat. No. 4,944,298 (Sholder). For a more detailed description of the various timing intervals used within the pacing device and their inter-relationship, see U.S. Pat. No. 4,788,980 (Mann et. al.). The '052, '555, '298 and '980 patents are incorporated herein by reference.

Depending on implementation, the device 710 can be capable of treating both fast and slow arrhythmias with stimulation therapy, including pacing, cardioversion and defibrillation stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with pacing, cardioversion and defibrillation stimulation. For example, where the implantable device is a monitor that does not provide any therapy, it is clear that many of the blocks shown may be eliminated.

The housing 740, shown schematically in FIG. 8, is often referred to as the "can", "case" or "case electrode" and may be programmably selected to act as the return electrode for all "unipolar" modes. The housing 740 may further be used as a return electrode alone or in combination with one or more of the coil electrodes, 728, 736 and 738, for shocking purposes. The housing 740 can further include a connector (not shown) having a plurality of terminals, 842, 844, 846, 848, 852, 854, 856, and 858 (shown schematically and, for convenience, the names of the electrodes to which they are connected are shown next to the terminals). As such, to achieve right atrial sensing and pacing, the connector includes at least a right atrial tip terminal ($A_R$ TIP) 842 adapted for connection to the atrial tip electrode 722.

To achieve left atrial and ventricular sensing, pacing and shocking, the connector includes at least a left ventricular tip terminal ($V_L$ TIP) 844, a left atrial ring terminal ($A_L$ RING) 846, and a left atrial shocking terminal ($A_L$ COIL) 848, which are adapted for connection to the left ventricular ring electrode 726, the left atrial tip electrode 727, and the left atrial coil electrode 728, respectively.

To support right ventricle sensing, pacing and shocking, the connector further includes a right ventricular tip terminal ($V_R$ TIP) 852, a right ventricular ring terminal ($V_R$ RING) 854, a right ventricular shocking terminal ($R_V$COIL) 856, and an SVC shocking terminal (SVC COIL) 858, which are adapted for connection to the right ventricular tip electrode 732, right ventricular ring electrode 734, the RV coil electrode 726, and the SVC coil electrode 738, respectively.

An atrial pulse generator 870 and a ventricular pulse generator 872 generate pacing stimulation pulses for delivery by the right atrial lead 720, the right ventricular lead 730, and/or the coronary sinus lead 724 via an electrode configuration switch 874. It is understood that in order to provide stimulation therapy in each of the four chambers of the heart, the atrial and ventricular pulse generators, 870 and 872, may include dedicated, independent pulse generators, multiplexed pulse generators, or shared pulse generators. The pulse generators, 870 and 872, are controlled by the microcontroller 860 via appropriate control signals, 876 and 878, respectively, to trigger or inhibit the stimulation pulses.

The microcontroller 860 further includes timing control circuitry 879 which is used to control pacing parameters (e.g., the timing of stimulation pulses) as well as to keep track of the timing of refractory periods, noise detection windows, evoked response windows, alert intervals, marker channel timing, etc., which is well known in the art. Examples of pacing parameters include, but are not limited to, atrio-ventricular delay, interventricular delay and interatrial delay.

The switch bank 874 includes a plurality of switches for connecting the desired electrodes to the appropriate I/O circuits, thereby providing complete electrode programmability. Accordingly, the switch 874, in response to a control signal 880 from the microcontroller 860, determines the polarity of the stimulation pulses (e.g., unipolar, bipolar, etc.) by selectively closing the appropriate combination of switches (not shown) as is known in the art.

Atrial sensing circuits 882 and ventricular sensing circuits 884 may also be selectively coupled to the right atrial lead 720, coronary sinus lead 724, and the right ventricular lead 730, through the switch 874 for detecting the presence of cardiac activity in each of the four chambers of the heart. Accordingly, the atrial (ATR. SENSE) and ventricular (VTR. SENSE) sensing circuits, 882 and 884, may include dedicated sense amplifiers, multiplexed amplifiers, or shared amplifiers. The switch 874 determines the "sensing polarity" of the cardiac signal by selectively closing the appropriate switches, as is also known in the art. In this way, the clinician may program the sensing polarity independent of the stimulation polarity.

Each sensing circuit, 882 and 884, preferably employs one or more low power, precision amplifiers with programmable gain and/or automatic gain control, bandpass filtering, and a threshold detection circuit, as known in the art, to selectively sense the cardiac signal of interest. The automatic gain control enables the device 710 to deal effectively with the difficult problem of sensing the low amplitude signal characteristics of atrial or ventricular fibrillation. Such sensing circuits, 882 and 884, can be used to determine cardiac performance values used in the present invention. Alternatively, an automatic sensitivity control circuit may be used to effectively deal with signals of varying amplitude.

The outputs of the atrial and ventricular sensing circuits, 882 and 884, are connected to the microcontroller 860 which, in turn, are able to trigger or inhibit the atrial and ventricular pulse generators, 870 and 872, respectively, in a demand fashion in response to the absence or presence of cardiac activity, in the appropriate chambers of the heart. The sensing circuits, 882 and 884, in turn, receive control signals over signal lines, 886 and 888, from the microcontroller 860 for purposes of measuring cardiac performance at appropriate times, and for controlling the gain, threshold, polarization charge removal circuitry (not shown), and timing of any blocking circuitry (not shown) coupled to the inputs of the sensing circuits, 882 and 886.

For arrhythmia detection, the device 710 includes an arrhythmia detector 862 that utilizes the atrial and ventricular sensing circuits, 882 and 884, to sense cardiac signals to determine whether a rhythm is physiologic or pathologic. The timing intervals between sensed events (e.g., P-waves, R-waves, and depolarization signals associated with fibrillation) can be classified by the microcontroller 860 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to assist with determining the type of remedial therapy that is needed (e.g., bradycardia pacing, anti-tachycardia pacing, cardioversion shocks or defibrillation shocks, collectively referred to as "tiered therapy"). Additionally, the arrhythmia detector 862 can perform arrhythmia discrimination, e.g., using measures of arterial blood pressure determined in accordance with embodiments of the present invention. Exemplary details of such arrhythmia discrimination, including tachyarrhythmia classification, are discussed above. The arrhythmia detector 862 can be implemented within the microcontroller 860, as shown in FIG. 8. Thus, this detector 862 can be implemented by software, firmware, or combinations thereof. It is also possible that all, or portions, of the arrhythmia detector 862 can be implemented using hardware. Further, it is also possible that all, or portions, of the arrhythmia detector 862 can be implemented separate from the microcontroller 860.

In accordance with embodiments of the present invention, the implantable device 710 includes a MI monitor 867, which can monitor for an impending MI using the techniques described above with reference to FIGS. 1-6. The MI monitor 867 can be implemented within the microcontroller 860, as shown in FIG. 8, and can be implemented by software, firmware, or combinations thereof. It is also possible that all, or portions, of the MI monitor 867 to be implemented using hardware. Further, it is also possible that all, or portions, of the MI monitor 867 to be implemented separate from the microcontroller 860. The MI monitor 867 can be used in a closed loop control system to detect, recognize and treat a patient before a blockage of a coronary artery occurs. FIG. 8 also shows a patient alert 819 that can be triggered, e.g., at steps 108 and/or 616 described above with reference to FIGS. 1 and 6.

The implantable device 710 can also include a pacing controller 866, which can adjust a pacing rate and/or pacing intervals based on measures of arterial blood pressure, in accordance with embodiments of the present invention. The pacing controller 866 can be implemented within the microcontroller 860, as shown in FIG. 8. Thus, the pacing controller 866 can be implemented by software, firmware, or combinations thereof. It is also possible that all, or portions, of the pacing controller 866 can be implemented using hardware. Further, it is also possible that all, or portions, of the pacing controller 866 can be implemented separate from the microcontroller 860.

The implantable device can also include a medication pump 803, which can deliver medication to a patient if an impending MI is detected. Information regarding implantable medication pumps may be found in U.S. Pat. No. 4,731,051 (Fischell) and in U.S. Pat. No. 4,947,845 (Davis), both of which are incorporated by reference herein.

Still referring to FIG. 8, cardiac signals are also applied to the inputs of an analog-to-digital (A/D) data acquisition system 890. The data acquisition system 890 is configured to acquire IEGM and/or ECG signals, convert the raw analog data into a digital signal, and store the digital signals for later processing and/or telemetric transmission to an external device 802. The data acquisition system 890 can be coupled to the right atrial lead 720, the coronary sinus lead 724, and the right ventricular lead 730 through the switch 874 to sample cardiac signals across any pair of desired electrodes. In specific embodiments, the data acquisition system 890 may be used to acquire IEGM signals for the analysis of changes in the ST-segment for detecting myocardial ischemia, and for monitoring PWV, DBP and HR.

The data acquisition system 890 can be coupled to the microcontroller 860, or other detection circuitry, for detecting an evoked response from the heart 712 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 860 detects a depolarization signal during a window following a stimulation pulse, the presence of which indicates that capture has occurred. The microcontroller 860 enables capture detection by triggering the ventricular pulse generator 872 to generate a stimulation pulse, starting a capture detection window using the timing control circuitry 879 within the microcontroller 860, and enabling the data acquisition system 890 via control signal 892 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

The microcontroller 860 is further coupled to the memory 894 by a suitable data/address bus 896, wherein the programmable operating parameters used by the microcontroller 860 are stored and modified, as required, in order to customize the operation of the implantable device 710 to suit the needs of a particular patient. Such operating parameters define, for example, pacing pulse amplitude, pulse duration, electrode polarity, rate, sensitivity, automatic features, arrhythmia detection criteria, and the amplitude, wave shape and vector of each shocking pulse to be delivered to the patient's heart 712 within each respective tier of therapy. The memory 894 can also store data about area under the curve and/or number of inflection points in a plethysmography signal and baseline information useful for monitoring for an impending MI.

The operating parameters of the implantable device 710 may be non-invasively programmed into the memory 894 through a telemetry circuit 801 in telemetric communication with an external device 802, such as a programmer, transtelephonic transceiver, or a diagnostic system analyzer. The telemetry circuit 801 can be activated by the microcontroller 860 by a control signal 806. The telemetry circuit 801 advantageously allows intracardiac electrograms and status information relating to the operation of the device 710 (as contained in the microcontroller 860 or memory 894) to be sent to the external device 802 through an established communication link 805. The telemetry circuit can also be used to transmit data relating to a predicted impending MI to the external device 802.

For examples of telemetry devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734 entitled "Efficient Generation of Sensing Signals in an Implantable Medical Device such as a Pacemaker or ICD" (McClure et al.), which patents are hereby incorporated herein by reference.

The implantable device 710 additionally includes a battery 811 which provides operating power to all of the circuits shown in FIG. 8. If the implantable device 710 also employs shocking therapy, the battery 811 should be capable of operating at low current drains for long periods of time, and then be capable of providing high-current pulses (for capacitor charging) when the patient requires a shock pulse. The battery 811 should also have a predictable discharge characteristic so that elective replacement time can be detected.

The implantable device 710 can also include a magnet detection circuitry (not shown), coupled to the microcontroller 860. It is the purpose of the magnet detection circuitry to detect when a magnet is placed over the implantable device 710, which magnet may be used by a clinician to perform various test functions of the implantable device 710 and/or to signal the microcontroller 860 that the external programmer 802 is in place to receive or transmit data to the microcontroller 860 through the telemetry circuits 801.

As further shown in FIG. 8, the device 710 is also shown as having an impedance measuring circuit 813 which is enabled by the microcontroller 860 via a control signal 814. The known uses for an impedance measuring circuit 813 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds and heart failure condition; detecting when the device has been implanted; measuring stroke volume; and detecting the opening of heart valves, etc. The impedance measuring circuit 813 is advantageously coupled to the switch 874 so that any desired electrode may be used. The impedance measuring circuit 813 can be used to obtain an impedance plethysmography (IPG) signal, which can be used in certain embodiments of the present invention.

In the case where the implantable device 710 is also intended to operate as an implantable cardioverter/defibrillator (ICD) device, it should detect the occurrence of an arrhythmia, and automatically apply an appropriate electrical shock therapy to the heart aimed at terminating the detected arrhythmia. To this end, the microcontroller 860 further controls a shocking circuit 816 by way of a control signal 818. The shocking circuit 816 generates shocking pulses of low (up to 0.5 Joules), moderate (0.6-10 Joules), or high energy (11 to 40 Joules), as controlled by the microcontroller 860. Such shocking pulses are applied to the patient's heart 712 through at least two shocking electrodes, and as shown in this embodiment, selected from the left atrial coil electrode 728, the RV coil electrode 736, and/or the SVC coil electrode 738. As noted above, the housing 740 may act as an active electrode in combination with the RV electrode 736, or as part of a split electrical vector using the SVC coil electrode 738 or the left atrial coil electrode 728 (i.e., using the RV electrode as a common electrode).

The above described implantable device 710 was described as an exemplary pacing device. One or ordinary skill in the art would understand that embodiments of the present invention can be used with alternative types of implantable devices. Accordingly, embodiments of the present invention should not be limited to use only with the above described device.

The present invention has been described above with the aid of functional building blocks illustrating the performance of specified functions and relationships thereof. The boundaries of these functional building blocks have often been arbitrarily defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in the flow diagrams. Further, it may be possible to change the order of some of the steps shown in flow diagrams, without substantially changing the overall events and results. For another example, it is possible to change the boundaries of some of the blocks shown in FIG. 8.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed is:

1. For use with a chronically implanted device, a method for monitoring for an impending myocardial infarction (MI), comprising:
   (a) obtaining
      a first signal indicative of changes arterial volume, the first signal comprising one of a photoplethysmography (PPG) signal or an impedance-plethysmography (IPG) signal, and
      a second signal indicative of electrical cardiac activity, the second signal comprising one of an electrocardiogram (ECG) signal or an intracardiac electrogram (IEGM) signal;
   (b) determining, based on the first and second signals, a metric indicative of aortic pulse wave velocity (PWV);
   (c) determining, based on the first signal, a metric indicative of diastolic blood pressure (DBP);
   (d) determining, based on at least one of the first and or second signals, a metric indicative of heart rate (HR);
   (e) determining, based on the first signal, a metric indicative of vascular stiffness (VS) by determining a measure of a number of inflections in the first signal, wherein a greater the measure of the number of inflections in the first signal a greater the vascular stiffness;
   (f) monitoring for an impending MI based on the metrics indicative of PWV, DBP, HR and VS, wherein an increase in each of the metrics indicative of PWV, DBP, HR and VS is interpreted as an increase in a risk of an impending MI; and
   (g) triggering an alert and/or therapy in response to an impending MI being detected at step (f);
      wherein one or more of steps (b) through (g) is/are performed using a processor.

2. The method of claim 1, wherein step (f) comprises detecting an impending MI if the metrics indicative of PWV, DBP, HR and VS each satisfies a corresponding criteria indicative of an impending MI.

3. The method of claim 1, wherein step (f) comprises detecting an impending MI if a majority of the metrics indicative of PWV, DBP, HR and VS each satisfies a corresponding criteria indicative of an impending MI.

4. The method of claim 1, wherein:
   the first signal indicative of changes arterial volume, that is obtained at step (a), is a photoplethysmography (PPG) signal; and
   step (e) comprises determining, based on the PPG signal, a metric indicative of vascular stiffness (VS) by determining a measure of a number of inflections in the PPG signal, wherein a greater the measure of the number of inflections in the PPG signal a greater the vascular stiffness.

5. The method of claim 1, wherein:
   the first signal indicative of changes arterial volume, that is obtained at step (a), is an impedance-plethysmography (IPG) signal; and
   step (e) comprises determining, based on the IPG signal, a metric indicative of vascular stiffness (VS) by determining a measure of a number of inflections in the IPG signal, wherein a greater the measure of the number of inflections in the IPG signal a greater the vascular stiffness.

6. A system for monitoring for an impending myocardial infarction (MI), comprising:
   a sensor configured to produce a first signal that is indicative of changes in arterial volume;
   one or more electrodes to produce a second signal indicative of electrical cardiac activity, the second signal comprising one of an electrocardiogram (ECG) signal or an intracardiac electrogram (IEGM) signal; and
   a monitor configured to
      determine, based on the first and second signals, a metric indicative of aortic pulse wave velocity (PWV);
      determine, based on the first signal, a metric indicative of diastolic blood pressure (DBP);
      determine, based on at least one of the first and second signals, a metric indicative of heart rate (HR);
      determine, based on the first signal, a metric indicative of vascular stiffness (VS) by determining a measure of a number of inflections in the first signal, wherein a greater the measure of the number of inflections in the first signal a greater the vascular stiffness;

monitor for an impending MI based on the metrics indicative of PWV, DBP, HR and VS, wherein an increase in each of the metrics indicative of PWV, DBP, HR and VS is interpreted as an increase in a risk of an impending MI; and trigger an alert and/or therapy in response to an impending MI being detected.

7. The system of claim 6, wherein the monitor is configured to detect an impending MI if the metrics indicative of PWV, DBP, HR and VS each satisfies a corresponding criteria indicative of an impending MI.

8. The system of claim 6, wherein the monitor is configured to detect an impending MI if a majority of the metrics indicative of PWV, DBP, HR and VS each satisfies a corresponding criteria indicative of an impending MI.

9. The system of claim 6, wherein:

the first signal indicative of changes arterial volume, that is obtained by the sensor, is a photoplethysmography (PPG) signal; and the monitor is configured to determine, based on the PPG signal, a metric indicative of vascular stiffness (VS) by determining a measure of a number of inflections in the PPG signal, wherein a greater the measure of the number of inflections in the PPG signal a greater the vascular stiffness.

10. The system of claim 6, wherein:

the first signal indicative of changes arterial volume, that is obtained by the sensor, is an impedance-plethysmography (IPG) signal; and the monitor is configured to determine, based on the IPG signal, a metric indicative of vascular stiffness (VS) by determining a measure of a number of inflections in the IPG signal, wherein a greater the measure of the number of inflections in the IPG signal a greater the vascular stiffness.

* * * * *